(12) United States Patent
Beck et al.

(10) Patent No.: US 6,223,075 B1
(45) Date of Patent: Apr. 24, 2001

(54) IONTOPHORETIC DELIVERY DEVICE WITH INTEGRAL HYDRATING MEANS

(75) Inventors: Jon E. Beck, Salt Lake City; Lindsay B. Lloyd, West Jordan; Tomasz J. Petelenz, Salt Lake City, all of UT (US)

(73) Assignee: Iomed, Inc., Salt Lake City, UT (US)

( * ) Notice: Subject to any disclaimer, the term of this patent is extended or adjusted under 35 U.S.C. 154(b) by 0 days.

(21) Appl. No.: 08/762,051

(22) Filed: Dec. 9, 1996

Related U.S. Application Data

(63) Continuation of application No. 08/293,484, filed on Aug. 22, 1994, now abandoned.

(51) Int. Cl.$^7$ .................................................... A61N 1/30
(52) U.S. Cl. ........................... 604/20; 383/210; 383/211; 222/541.9; 607/153
(58) Field of Search ................................... 383/210, 211; 222/94, 541.6, 541.9; D24/189; 602/48; 604/20, 87, 410, 416, 244, 890.1; 607/149–153; 424/447–449

(56) References Cited

U.S. PATENT DOCUMENTS

| | | | |
|---|---|---|---|
| 2,702,146 | * | 2/1955 | Land .................................. 222/541.6 |
| 3,754,700 | * | 8/1973 | Bonk .................................... 383/210 |
| 4,383,529 | | 5/1983 | Webster ................................ 604/20 |
| 4,941,574 | * | 7/1990 | Meehan ................................ 383/210 |
| 5,281,287 | | 1/1994 | Lloyd et al. ........................... 156/80 |
| 5,288,289 | | 2/1994 | Haak et al. ............................ 604/20 |
| 5,310,404 | * | 5/1994 | Gyory et al. ......................... 607/153 |
| 5,320,598 | | 6/1994 | Haak et al. ............................. 604/20 |

FOREIGN PATENT DOCUMENTS

| | | | |
|---|---|---|---|
| 2066208 | * | 7/1981 | (GB) .................................. 383/211 |
| WO 93/24177 | | 12/1993 | (WO) . |

* cited by examiner

*Primary Examiner*—Mark Bockelman
(74) *Attorney, Agent, or Firm*—Factor & Partners

(57) ABSTRACT

The present invention provides methods and apparatus permitting rapid and thorough hydration of an initially dry hydratable matrix element contained within an iontophoretic bioelectrode. The apparatus of the invention comprises a bioelectrode system for iontophoretic delivery of medicaments having at least one hydratable matrix element and associated removable hydration assembly. The preferred embodiment of the present invention comprises two hydratable matrix elements each having an associated removable hydration assembly and each being associated with an electrical current distribution element. The removable hydration assembly includes an initially sealed liquid-storage component which maintains the desired hydrating liquid in isolation from the hydratable matrix element until such time as hydration is desired. At that time, the removable hydration assembly can be activated by the user through application of force to an extending tab member attached to the sealed liquid-storage component thereby causing progressive unsealing of the sealed liquid-storage component and progressively depositing the hydrating liquid uniformly onto the entire surface of the hydratable matrix element. Following hydration of the matrix element, the spent hydration assembly can be withdrawn completely from within the bioelectrode system.

9 Claims, 7 Drawing Sheets

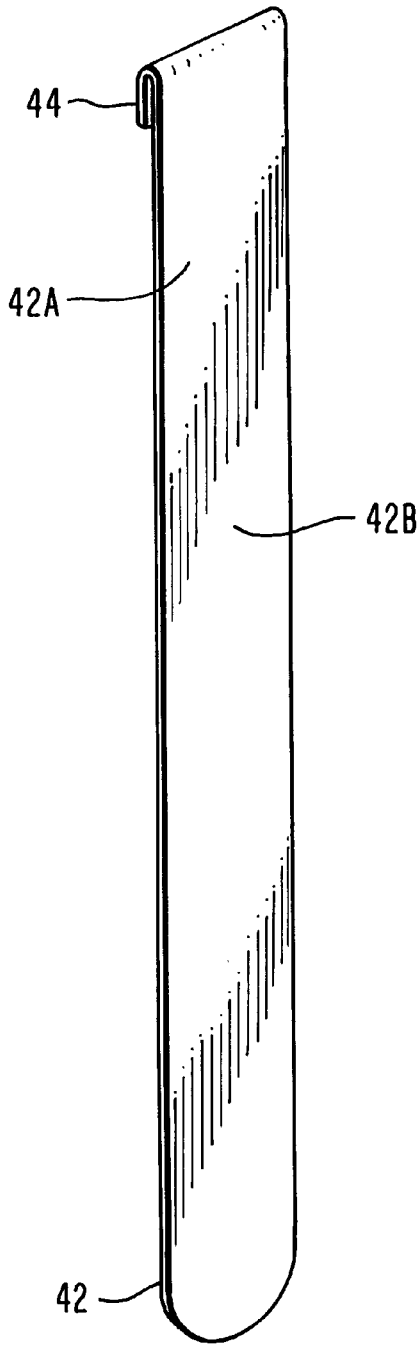
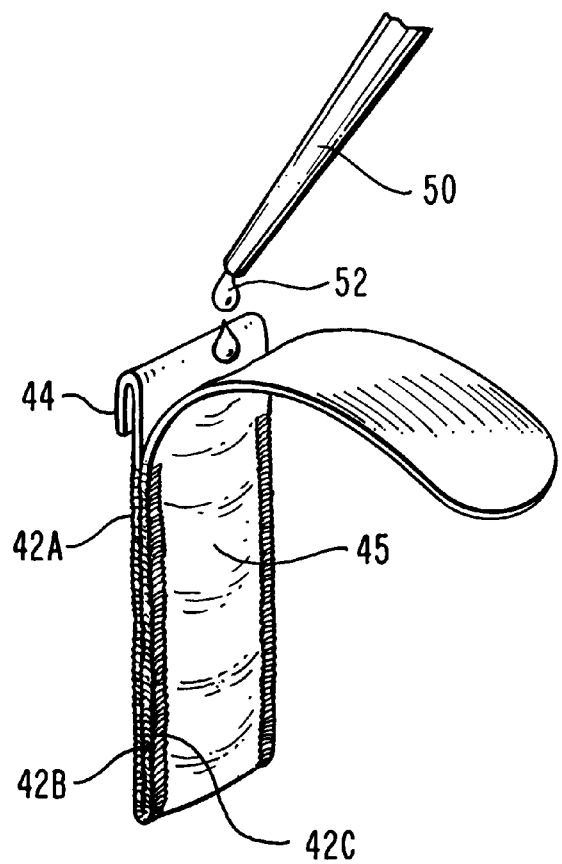
FIG. 7
FIG. 8

IONTOPHORETIC DELIVERY DEVICE WITH INTEGRAL HYDRATING MEANS

This application is a continuation of U.S. application Ser. No. 08/293,484, filed Aug. 22, 1994, now abandoned.

BACKGROUND OF THE INVENTION

1. Technical Field

This invention relates to a bioelectrode system for iontophoretic delivery of medicaments.

2. Background Information

Iontophoretic delivery of medicaments has been found useful in a number of different applications including, for example, delivery of pilocarpine salts as a diagnostic test for cystic fibrosis and delivery of lidocaine hydrochloride to anesthetize a localized area prior to some minor surgical procedure such as wart removal.

Typically, systems for iontophoretic delivery of medicaments use two bioelectrodes, one positive and one negative, each placed in electrical contact with a portion of the skin or a mucosal surface of the body. Also typical is that each bioelectrode contains an electrolyte solution at least one of which contains ionized medicament. An electrical power source, such as a battery, is connected to the electrodes to complete the electrical circuit through the body. The charge of the ionized solution determines bioelectrode polarity such that, when current is supplied, the medicament ions migrate away from the electrode and are thereby delivered through the skin.

Some type of enclosure or other fluid-holding means is typically used to contain the ionized electrolyte or medicament solution such that a mechanism or structure on the enclosure is necessary to permit the introduction of solution thereunto. Such structure has typically included some type of orifice containing a plug into which a hypodermic needle or syringe canula may be inserted to allow delivery of the solution through the orifice into the interior of the enclosure, while preventing the outflow of the solution after it has been introduced into the enclosure. The requirement of such solution receiving mechanism or enclosure increases the cost of the bioelectrode system and gives rise to potential spillage and leakage of solution. Such spillage and leakage can result in an inoperative or defective device.

More recent bioelectrode systems have used hydrophilic polymers to form means for holding the medicament and electrolyte solutions. See, for example, the preformed gel body described in U.S. Pat. No. 4,383,529 issued to Webster, incorporated herein by reference. Although such pre-hydrated gel bodies may prevent leakage and spillage problems, there may still be stability and storage problems. To address these problems, bioelectrodes containing initially "dry," but hydratable, holding means for the medicament and electrolyte solutions have been developed. See, for example, the hydratable layers of hydrogel sheets described in Lloyd et al., U.S. Pat. No. 5,236,412, incorporated herein by reference.

In addition, efforts have been directed to developing bioelectrode systems containing initially dry, but hydratable, solution-holding components wherein the means for hydrating the components is also self-contained. Thus, for example, Haak et al., U.S. Pat. No. 5,288,289 and Gyory et al., published international patent application, WO 93/24177, both of which are incorporated herein by reference, disclose various self-contained means for releasing hydrating liquid from liquid-storage components and thereby hydrating the initially dry solution-holding components.

In certain embodiments of the Haak patent, the hydrating liquid-storage components comprise breakable capsules filled with the desired hydrating liquid which are positioned within a layer of material such that the liquid is isolated from the hydratable solution-holding components. Squeezing or flexing of the hydrating liquid-storage component breaks the capsules and releases the hydrating liquid. The hydrating liquid flows onto the electrical current distribution element and through preformed passageways to the hydratable solution-holding component. Optional wicking material is described to enhance rapid transfer of the liquid across the electrode conductor surface where the liquid can flow through the passageways to the hydratable solution-holding component.

It can be seen that the hydrating rate, the completeness of the fluid transfer, and the fluid distribution pattern is affected by the characteristics and properties of the separate elements which must be in fluid communication, i.e., the interposed electrical current distribution element material, the hydrating liquid-storage component material, the hydratable solution-holding component material, and the optional wicking material. Other variables include the size, shape, and other characteristics of the flow through openings between the hydrating liquid-storage component and the hydratable solution-holding component, the distributional arrangement of the capsules within the hydrating liquid-storage component material, and even whether or not all of the capsules break or whether the encapsulated liquid is completely dispensed from the broken capsules. Moreover, inadvertent squeezing or flexing of the hydrating liquid-storage component could occur during manufacture, shipping, storing or handling of the device. Such an occurrence could break some or all of the hydrating liquid-filled capsules and cause premature hydration of the hydratable solution-holding component. Such premature hydration could result in an unusable or defective device.

Alternatively, the bioelectrode system disclosed in the Haak patent comprises separate components such that the hydrating liquid-storage component is covered by a removable liquid-impermeable sheet such that removal of the sheet exposes the hydrating liquid. The hydrating liquid-storage component is attached to one portion of the system. The hydratable solution-holding component is attached to a separate portion of the system. A user of the system removes the liquid-impermeable sheet to expose the hydrating liquid and then manually assembles the separate portions such that the hydrating fluid contacts, and thereby hydrates, the hydratable solution-holding component. Alternatively, the system portions are not separate from each other but, rather, the portion attached to the hydrating liquid-storage component is positioned adjacent to the portion attached to the hydratable solution-holding component such that a folding over maneuver will cause contact of the hydratable solution-holding component with the exposed hydrating fluid. Yet another embodiment has the hydrating liquid-storage component and the hydratable solution-holding component attached to a first portion of the system while a second portion of the system contains pins for puncturing the hydrating liquid-storage component. In this embodiment, manual alignment and assembly of the first and second portions causes the pins to puncture the hydrating liquid-storage component and thereby release the fluid to hydrate the hydratable solution-holding component.

In the above-described devices, the need to manually assemble the separate system portions inhibits inadvertent hydration of the hydratable solution-holding component. Nevertheless, separate, or foldable, portions are more costly and cumbersome to use than a unitary device. Such devices also depend on proper assembly by the user. Mis-alignment or improper use could result in inefficient hydration.

As with the previously discussed Haak embodiments, the hydrating rate, the completeness of the fluid transfer, and the uniformity of fluid distribution in the above-described devices are also affected by the characteristics and properties of the individual components, i.e., the interposed electrical current distribution element material, the hydratable solution-holding component material, the hydrating liquid-storage component material, and the optional wicking material. The precision of the alignment of the system portions with each other will also be a factor. In addition, specifically for the device featuring puncturing pins to release the hydrating liquid, the variability in size and shape of the resultant torn or punctured openings created within the hydrating liquid-storage component material or between the hydrating liquid-storage component and the hydratable solution-holding component will affect the escape and dispensing of the hydrating liquid.

Approaches disclosed by Gyory et al. include a hydrating liquid-storage component which is separated from a hydratable solution-holding component by a liquid-impermeable sheet. Certain embodiments rely on packaging means to protect from inadvertent release of the hydrating liquid and to cause "automatic" hydration upon removal of the device from the package. The packaging means which effect "automatic" hydration include compression means to rupture or burst the liquid-impermeable sheet; blade means to puncture the liquid-impermeable sheet; and pull-tab means to rip or tear the liquid-impermeable sheet. An alternative embodiment attaches the pull-tab means, for ripping or tearing the liquid-impermeable sheet, to a release liner covering a skin contacting surface of the device. In this embodiment, removal of the release liner prior to placement on the patient "automatically" pulls the pull-tab means to rip or tear the liquid-impermeable sheet and thereby release the hydrating liquid. Like the Haak invention, Gyory also discloses liquid flow control means for directing the flow of hydrating liquid through the breached liquid-impermeable sheet to the hydratable solution-holding component.

It can be seen that, in Gyory's devices, it is the liquid-impermeable sheet separating the hydrating liquid-storage component from the hydratable solution-holding component which is physically ruptured, punctured, or ripped. The material comprising the hydrating liquid-storage component, however, remains intact. After the liquid-impermeable sheet is breached and the hydrating liquid is released, the material which formed the now-depleted hydrating liquid-storage component remains positioned within the device. In the case of a ruptured or punctured sheet, all of the now-breached liquid-impermeable sheet material also remains entirely within the device. In the pull-tab embodiment, some of the sheet material is ripped or torn away and is removed from within the device with the attached pull-tab. Nevertheless, in all cases, a substantial portion of the liquid-impermeable sheet material as well as all of the hydrating liquid-storage component material remains within the device following the hydration process.

The rupturing, puncturing, or tearing of the liquid-impermeable sheet material exposes torn edges and, thus, inner layers, of the liquid-impermeable sheet including, for example, foil edges. The hydrating liquid-storage component material and the breached liquid-impermeable sheet material, including exposed torn inner layer edges, remain within the device. These no-longer needed materials could interfere with electrical current distribution. These materials also contact the now-hydrated solution-holding component such that deleterious communication with the solution is possible. For example, over long-term iontophoresis, i.e. many hours, materials such as exposed foil edges could corrode. Thus, it would be advantageous to be able to remove the materials associated with the hydrating liquid-storage component following the hydration process.

Both Haak and Gyory provide liquid-conveying pathways to distribute the hydrating liquid. Such liquid-conveying pathways, however, necessarily affect the transfer of the hydrating fluid because the rate and amount of fluid transferred is limited by the pathway configuration. It would, however, be advantageous to effect essentially uniform transfer of the hydrating fluid directly onto the surface of the hydratable reservoir element.

SUMMARY OF THE INVENTION

It is a primary object of the present invention to provide methods and apparatus permitting rapid and thorough hydration of an initially dry hydratable matrix element contained within an iontophoretic bioelectrode without requiring cumbersome manipulations or assembly of separate system portions of the bioelectrode. References to a matrix element will hereinafter be referred to as "hydratable" when used to indicate the initial "dry" state and as "hydrated" to indicate the state following hydration.

Another object of the present invention is to provide methods and apparatus utilizing a self-contained hydration assembly to permit thorough transfer and uniform and progressive distribution during the dispensing of substantially all of the desired hydrating liquid onto the hydratable matrix elements. The hydration assembly of the present invention advantageously ensures accurate achievement of desired ion concentrations and saturation of the hydratable matrix elements thus increasing the accuracy of calculated iontophoretically delivered medicament dosage.

Yet another object of the present invention is to provide methods and apparatus permitting complete removal of the spent hydration assembly from the bioelectrode system following the user-activated hydration process. In this manner, potential problems associated with the no-longer needed hydration assembly material remaining within the bioelectrode system, such as interference with conduction of the electrical current and deleterious interactions with the hydrated matrix elements, are avoided.

A further object of the present invention is to provide methods and apparatus utilizing a self-contained hydration assembly which is simple to operate and not subject to mis-alignment or mis-assembly by the user.

An additional object of the present invention is to provide an integral iontophoretic bioelectrode system which can be manufactured using existing equipment and techniques and having components which can be advantageously separately manufactured for subsequent assembly into an integral unit.

These and other objects and advantages of the invention will be better understood by reference to the detailed description, or will be appreciated by the practice of the invention.

To achieve the foregoing objects, and in accordance with the invention as embodied and broadly described herein, the apparatus of the invention comprises a bioelectrode system for iontophoretic delivery of medicaments having at least one hydratable matrix element and associated removable hydration assembly. The preferred embodiment of the present invention comprises two hydratable matrix elements each having an associated removable hydration assembly and each being associated with an electrical current distribution element. Typically, one matrix is associated with the positive electrical current distribution element and the other matrix is associated with the negative electrical current distribution element, although alternating current may also be utilized for certain applications.

The removable hydration assembly includes an initially sealed liquid-storage component which maintains the desired hydrating liquid in isolation from the hydratable matrix element until such time as hydration is desired. At that time, the removable hydration assembly can be activated by the user to cause progressive unsealing of the sealed liquid-storage component thereby progressively depositing the hydrating liquid uniformly onto the entire surface of the hydratable matrix element. This hydration process can be activated either prior to or following placement of the bioelectrode system on the patient's skin. Hydration following placement may be advantageous in that no fluid is lost through contact with other surfaces, such as the packaging material or the user's hands. In addition, the bioelectrode system may be more easily and securely positioned on the patient in the initial dry, rather than the hydrated, state.

Following hydration of the matrix element, the spent hydration assembly can be withdrawn completely from within the bioelectrode system thereby preventing further interaction with the remainder of the bioelectrode system.

The hydratable matrix elements and the associated hydration assemblies of the present invention may be conveniently attached to a multilaminate mounting element. The multilaminate mounting element may comprise one layer containing the positive and negative electrical current distribution elements. The multilaminate mounting element also may conveniently comprise another layer providing fixation means for attachment of the bioelectrode system to a body surface. Additionally, the multilaminate mounting element could include other layers such as a moisture barrier layer, an insulating layer, and a sealant layer.

The bioelectrode system of the present invention comprises an electrical power source and electronic controller. These can be optionally positioned in either direct or remote communication with the integral unit. The electronic controller may be reusable or replaceable after a predetermined number of uses or time period. The remainder of the bioelectrode system may be disposable after, for example, a predetermined time period. The electrical power source is preferably a disposable battery integrally attached to the multilaminate mounting element.

BRIEF DESCRIPTION OF THE DRAWINGS

In the accompanying drawings, which represent the best mode presently contemplated for carrying out the present invention:

FIG. 7 illustrates a strip element of the preferred embodiment.

FIG. 8 illustrates filling of the pocket member formed from portions of the strip element of the preferred embodiment.

DETAILED DESCRIPTION OF THE PREFERRED EMBODIMENTS

Figure 1:
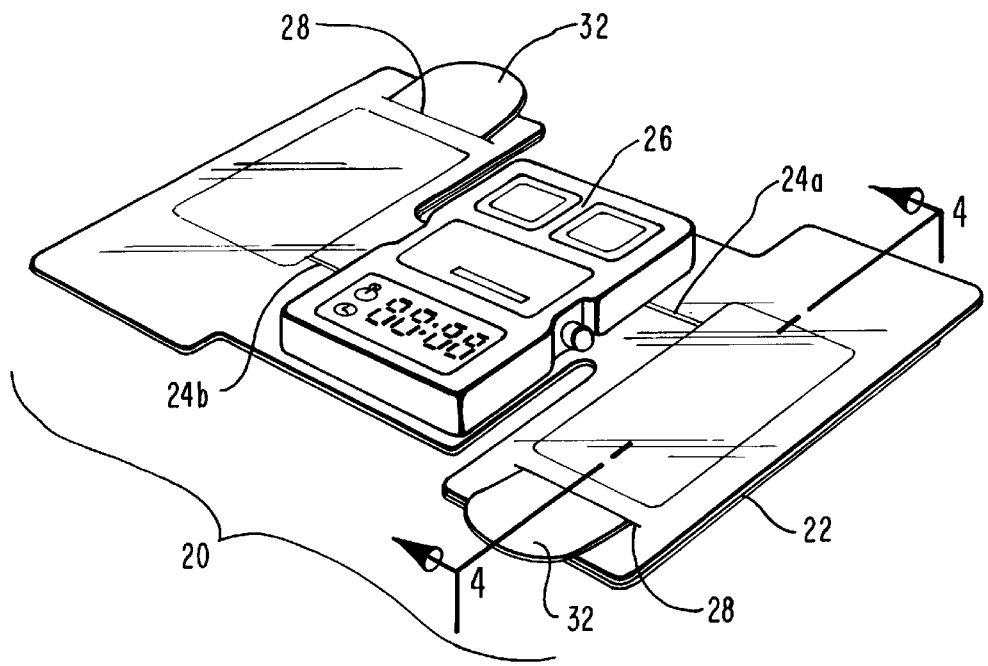
FIG. 1 is a perspective top view of a preferred embodiment of the bioelectrode system of the present invention.

The present invention relates to bioelectrode systems for iontophoretic delivery of medicaments. Iontophoresis is recognized as a useful process for the non-invasive transdermal or transmucosal delivery of beneficial agents. The presently preferred bioelectrode system of the present invention provides an integral unit that can be manufactured using conventional materials and techniques. Various components, such as the removable hydration assemblies, the hydratable matrix elements, the electronic controller, and the multilaminate mounting element incorporating the electronic distribution elements, can be conveniently manufactured separately and then delivered for final assembly into an integral unit. The integral bioelectrode unit of the present invention provides a compact, lightweight and simple to use device which can be adapted for use with various ionic chemical agents, hereinafter usually referred to as "medicaments." The teachings contained herein should also be understood, however, as also having applicability to single bioelectrodes and associated hydration systems.

The bioelectrode system of the present invention is generally intended to contain ionized medicament solution. A second hydratable matrix element is generally intended to contain a dispersive electrolyte solution. Initially, the matrix elements are "dry" such that the bioelectrode system can be stably stored and handled. The "dry" matrix elements are referred to as "hydratable" because they must be hydrated prior to use. Hydration is accomplished by means of a removable hydration assembly containing the desired hydrating liquid. Thus, the dry matrices may contain a dry form of the desired medicament or electrolyte solution which is hydrated with an appropriate diluent or the dry matrices may contain only support material which is hydrated with the appropriate medicament or electrolyte solution. It may also be possible to store and handle combinations of medicaments wherein some are stable in dry form and some are stable in hydrated form but the combination is not stable and must be kept separated prior to use. The stable dry medicaments can be stored in the dry matrix element and the stable hydrated medicaments can be stored in the hydrating fluid-storage component until the desired time of use.

Also integral to the presently preferred bioelectrode system of the present invention is a predetermined amount of hydrating liquid for each hydratable matrix element which is initially maintained in isolation from the hydratable matrix element. The present invention features an integral removable hydration assembly providing means for storing the hydrating liquid and dispensing the hydrating liquid onto the surface of the hydratable matrix element in a rapid and uniform manner at the time of iontophoresis. The hydration assembly is initially integral to the bioelectrode system of the present invention and comprises a predetermined amount of hydrating liquid isolated from the hydratable matrix element and stored within a sealed liquid-storage component. Following activation of the hydration assembly and completion of the hydration process, the entire hydration assembly is removable from within the bioelectrode system.

The presently preferred bioelectrode system is further designed to assure consistent dose control and even electrical current distribution with minimum power dissipation. Iontophoretic bioelectrode systems require an electrical power source. The electrical power source can be of any conventional type, although a compact, tamper-resistant, disposable battery which can be attached directly to the integral unit is preferred.

The bioelectrode system of the present invention can be easily applied to skin or mucosal body surfaces. The hydration process may be activated either prior to or following placement on the patient. Hydration following placement may be advantageous in that no fluid is lost through contact with other surfaces, such as the packaging material or the user's hands. In addition, the bioelectrode system may be more easily and securely positioned on the patient in the initial dry, rather than the hydrated, state. The compact and lightweight nature of the bioelectrode system permits comfortable wear for relatively long periods of time and placement of the system under clothing, if desired. The non-invasive nature of iontophoretic delivery avoids problems associated with other modes of administration such as delayed and erratic oral absorption or the discomfort and risks associated with injections or indwelling catheters.

It is presently preferred that an electronic controller be provided to control the conduct of iontophoresis. The electronic controller is preferably capable of monitoring the bioelectrode system with regard to duration, strength, polarity, and time profile or wave form of electric current flow, total dose of medicament administered, rate and timing of administered doses, calculated patient-specific blood concentration ranges, and related data. Recording, storing, and retrieval of such data could also be features of the electronic controller. The electronic controller is preferably compact and lightweight such that it can be attached directly to the bioelectrode system during use by a patient. Because it is not a low cost item, however, a directly attached electronic controller should be removable so that it can be re-used. Alternatively, the electronic controller may be attached to the bioelectrode system via remote communication means, preferably wireless. The electronic controller is preferably battery-powered such that the bioelectrode system is entirely portable.

The electronic controller is preferably designed to be programmable to achieve desired rates of medicament administration. For example, the bioelectrode system of the present invention could be used to provide a non-invasive transdermal, iontophoretic drug delivery system for patient-controlled administration of an opioid analgesic for control of severe pain such as, for example, postoperative pain. Examples of suitable medicaments for this purpose would include salts of fentanyl or sufentanil. A particularly preferred medicament is fentanyl hydrochloride.

Advantages of patient-controlled analgesia observed with currently utilized intravenous delivery devices include improved management of pain, lower incidence of pain-related morbidity, more efficient use of narcotics such that lower total doses are possibly used, shortened hospital stays, earlier ambulation, and reduced costs as compared to other pain control methods. Because iontophoretic delivery is non-invasive, however, the problems and risks associated with prolonged intravenous administration, such as discomfort and potential infections, are avoided.

The method of using the bioelectrode system of the present invention for delivery of patient-controlled analgesia includes programming the electronic controller to provide a dose range and administration pattern suitable for the particular patient. This step is preferably performed by an appropriate medical care provider. The electronic controller would be programmed to provide continuous baseline delivery of drug with low level current for a predetermined period of time. Thus, the bioelectrode system of the present invention would deliver a predetermined, individualized dose of narcotic analgesic in a continuous manner to assure appropriate steady-state plasma level of the narcotic. In addition, the patient would be able to administer additional bolus doses of drug with high level current over short periods for treatment of breakthrough pain. A lock-out time range could be adjusted by the medical provider to individualize the dose and rate of administration of the bolus doses.

Additional safety features could also be included. For example, when used for patient-controlled analgesia administration, activation of the bolus drug administration will be accessible to the patient yet protected from inadvertent activation, the electronic controller will not allow for interchanging electrodes between patients during treatment, and detachment or re-attachment of the controller during treatment will not interfere with the lock-out time and sequencing of bolus doses to prevent administration of excessive bolus doses. The controller could also include a bioelectrode recognition feature for identifying a specific bioelectrode upon disconnection such that the possibility of reconnecting to a different device and thereby confusing two different treatment protocols is eliminated.

A feature of the bioelectrode system of the present invention is that the system is stored in an initially "dry" state to avoid problems associated with the manufacture, storage, handling, stability, and use of pre-hydrated bioelectrodes. Another feature of the present invention is provision of self-contained means for hydrating an associated hydratable matrix element, which hydrated matrix element will serve as a medicament or electrolyte solution reservoir during iontophoresis. The hydrating means includes a removable hydration assembly containing an initially sealed liquid-storage component which isolates a pre-determined quantity of hydrating liquid from the hydratable matrix element until such time as hydration is desired.

In addition to being simple to use, an advantage of the present invention is that the self-contained hydrating means cannot be inadvertently activated. Yet, when desired, user activation of the self-contained hydrating means results in rapid, complete, and uniform transfer of the desired hydrating liquid onto the entire surface of the hydratable matrix element.

In the accompanying drawings, FIG. 1 illustrates a presently preferred integral bioelectrode system 20 constructed in accordance with the present invention. The bioelectrode system of the present invention is preferably a compact, lightweight, and largely disposable integral unit. First and second electrical current distribution elements 24a and 24b are preferably formed by depositing a conductive material onto a suitable backing thereby forming an electrode layer which can be incorporated within a multilaminate mounting element 22.

For example, the electrical current distribution elements may be formed of a metal foil, conductive carbon, or metal deposited or painted on a suitable backing. Examples of suitable materials include silver, zinc, silver/silver chloride, aluminum, platinum, stainless steel, gold, conductive carbon compounds and titanium. Alternatively, the electrical current distribution element layer could be formed of a conductive filler supported by a polymer matrix. The active surface area for each electrical current distribution element should preferably correspond to the surface area of the respective associated hydratable matrix element and should preferably comprise a surface area of about 8 $cm^2$.

In addition to providing support for the electrode layer comprising the first and second electrical current distribution elements 24a and 24b, the multilaminate mounting element 22 preferably serves as a support for various other components of the integral bioelectrode system. As illustrated in FIG. 1, electronic controller 26 is preferably attached to the multilaminate mounting element. The overall size of multilaminate mounting element 22 is preferably no larger than about 60 $cm^2$ such that the bioelectrode system is compact and lightweight.

The multilaminate mounting element preferably comprises additional layers such as a foil layer, electrically insulated from the electrical current distribution element, to provide a moisture barrier to inhibit evaporation of solution from the hydrated matrix elements during extended treatment periods. The insulation for the moisture barrier layer is preferably provided by an insulation layer comprising a polymer, such as a polyolefin/polyester composition. The multilaminate mounting element may also comprise a sealant layer, such as a polyolefin, applied to one surface. An example of a suitable flexible, heat sealable, barrier material suitable for use as the multilaminate mounting element is Techni-Lam Foil Lamination, #B-131 Prop, available from Technipaq, Inc., Crystal Lake, Ill.

Also shown in FIG. 1 is tab member 32 and cut-out slot 28. These features are described in detail below.

Figure 2:
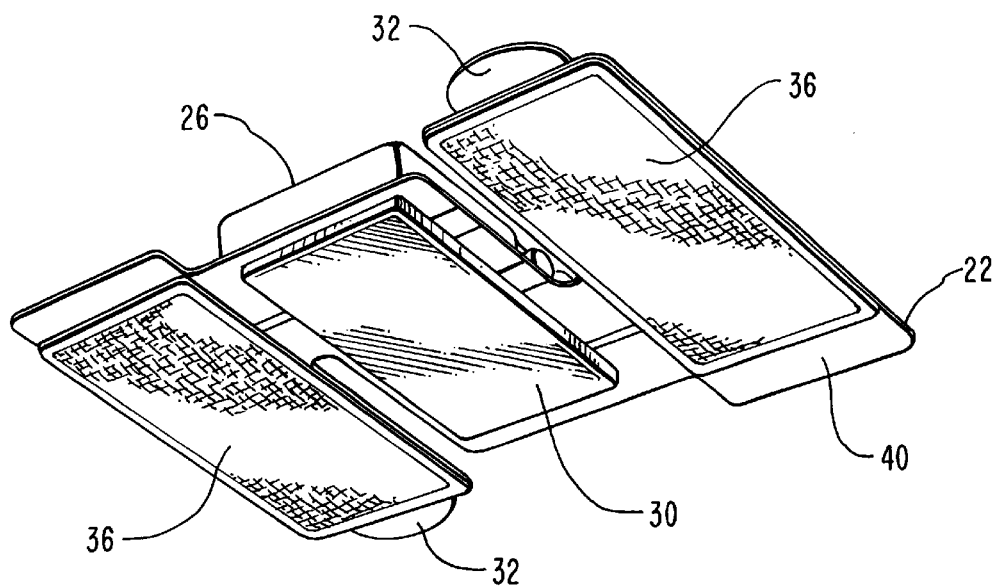
FIG. 2 is a perspective bottom view of the preferred embodiment of FIG. 1.

FIG. 2 illustrates the preferred embodiment of FIG. 1 viewed from the body-surface contacting side. In order to secure the bioelectrode system 20 to a patient's skin or mucosal surface, the body-contacting side of the preferred embodiment comprises fixation means. The fixation means preferably comprise a fixation layer 40 on the surface of the multilaminate mounting element. The portion of the fixation layer available for contacting the body surface should be of sufficient size to securely hold the bioelectrode system in place. The fixation layer can comprise, for example, a non-conducting adhesive layer. Such an adhesive layer is typically covered with a strippable release liner which is removed just prior to use.

Also shown in FIG. 2 are optional porous cover membranes 36 which preferably enclose the body-contacting surface of the hydratable matrix element. The porous cover membrane is not intended to limit the flux of ions but rather is intended to inhibit bulk fluid flow from the hydrated matrix during periods when the bioelectrode system is not positioned in contact with a body surface. Accordingly, suitable materials for the cover membrane preferably have the following properties: high flow rate, flexibility, hydrophilicity, inertness, and toughness. Practical choices include expanded and supported acrylic, polysulfone, PVDF, PTFE, PP or nylon membranes treated to be hydrophilic. Alternatively, a thin mesh or weave comprised of any of the above-identified polymers or of polyester could be used. The presently-preferred material for the cover membrane is Versapor 10000 which comprises an expanded acrylic with fibrous nylon support having pores of 10 microns. Versapor 10000 is available from Gelman Sciences, Membrane and Device Division, 600 South Wagner Road, Ann Arbor, Mich.

Also illustrated in FIG. 2 is a battery 30 which provides the electrical power source in the preferred embodiment. The battery is preferably a small, low-profile battery which is secured directly to the multilaminate mounting element 22. An example of a suitable battery is a flat-pac battery available from Gould Powerdex, Eastlake, Ohio.

The bioelectrode system of the present invention preferably permits the ionic medicament solution to be interposed between the appropriate electrical current distribution element and the patient's tissue such that the applied electrical current causes migration of the medicament ions into the tissue. Typically, one matrix is associated with the positive electrical current distribution element and the other matrix is associated with the negative electrical current distribution element, although alternating current may also be utilized for certain applications. As noted above, it is often disadvantageous to store a bioelectrode system with the medicament in hydrated form. Accordingly, it is preferred that medicament be provided in a dry form which permits hydration just prior to use.

Figure 3:
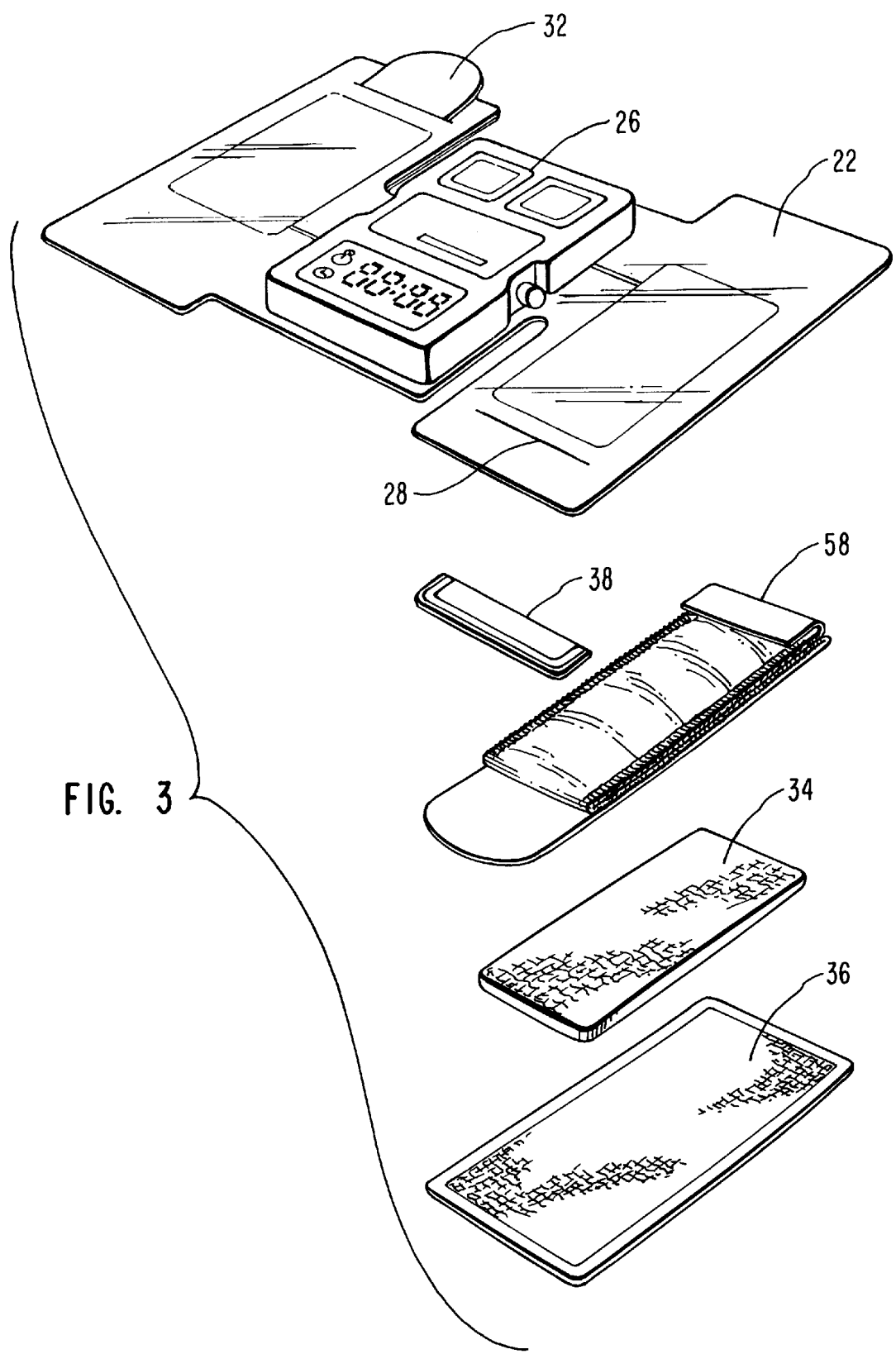
FIG. 3 is a perspective view of the preferred embodiment of FIG. 1 with certain components broken out and shown in order of attachment.

The bioelectrode system of the present invention contains hydratable matrix elements and self-contained means for hydration of the matrices just prior to use. FIG. 3 illustrates the preferred embodiment of the present invention with the components associated with one of the hydratable matrix elements 34 shown in broken out detail and in order of attachment to the multilaminate mounting element 22. A slot seal element 38 is a flap-type Reed seal that is positioned to align with the cut-out slot 28. Following hydration of the hydratable matrix and removal of the hydration assembly from within the bioelectrode system, slot seal element 38 advantageously functions to prevent the escape of medicament or electrolyte solution from the now-hydrated matrix element through the cut out slot during the period of iontophoresis.

Figure 13:
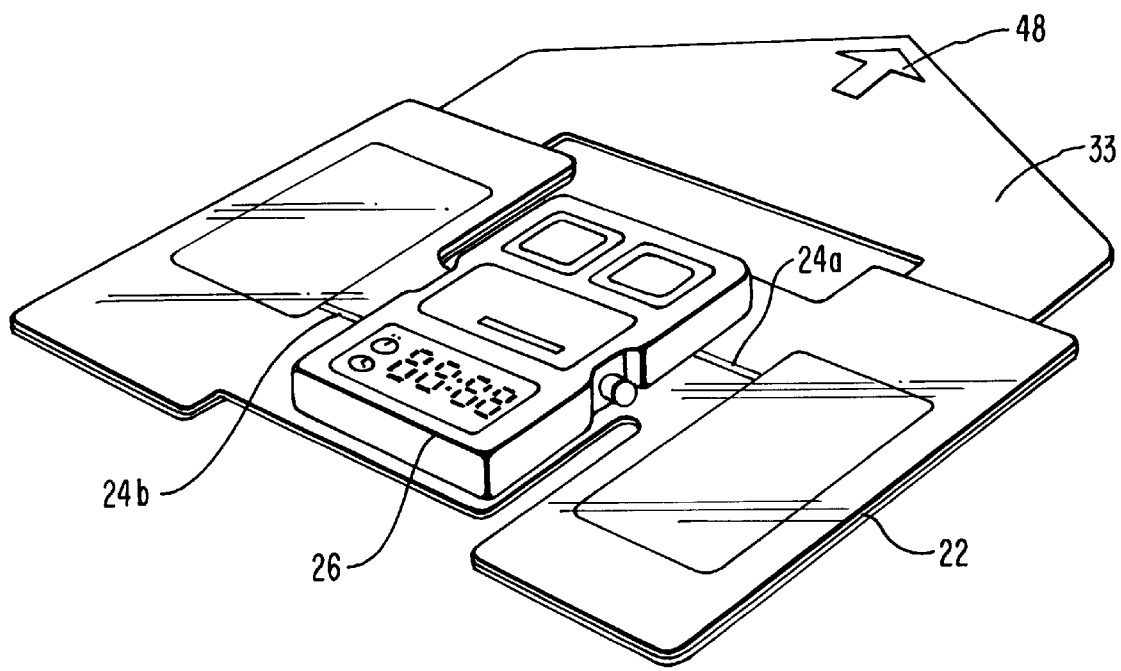
FIG. 13 is a perspective top view of another alternative embodiment of the present invention.

It should be understood that the slot seal element could alternatively be aligned with the cut-out slot but positioned between the hydration assembly 58 and the hydratable matrix element 34 rather than between the hydration assembly 58 and the multilaminate mounting element 22. Moreover, in the event that a cut-out slot was alternatively formed in the cover membrane instead of the multilaminate mounting element, the slot seal element could be positioned to function in the same manner and prevent communication between the hydrated matrix and the cut-out slot. Similarly, in an alternative embodiment, such as is illustrated in FIG. 13, wherein the tab member protrudes from between other components rather than through a cut-out slot, the slot seal element could be positioned to function in the same manner and prevent communication between the hydrated matrix and the opening through which the tab member had protruded and the hydration assembly had been withdrawn.

The hydratable matrix elements are designed to provide a suitable support matrix for either a dry form of medicament or a dry form of a dispersive electrolyte. The hydrated volume for each matrix element is preferably less than one milliliter of drug or electrolyte fluid. Preferably, the hydratable matrix elements comprise a support material suitable for impregnation with the desired medicament. Suitable support materials would include, for example, a polyurethane sponge such as Foamex felted Z-90 firmness 2 polyurethane foam or Foamex ACQUELL hydrophilic foam manufactured by Foamex Foam Inc.; a nonwoven polyester such as REEMAY; or a fiber or cloth material. It is generally desirable to load the hydratable matrix element with a hydrophilic thickener such as a high molecular weight polyethylene oxide (PEO), such as Polyox NF coagulant grade made by Union Carbide. Alternative hydrophilic materials include high molecular weight polyvinyl alcohol (PVA), poly-N-vinyl pyrrolidone (PVP), or other substituted pyrrolidones, polyacrylamide (PAAm), poly-N-isopropyl acrylamide (NIPPAm), polyhydroxyethyl methacrylate (PHEMA), or hydrophilic substituted HEMAs, polysaccharides such as agarose, hydroxyethyl cellulose (HEC), hydroxypropylmethyl cellulose (HPMC), hydroxypropyl cellulose (HPC), carboxymethyl cellulose (CMC), dextrans, modified starches, modified collagens, xanthan gum, guar gum, modified natural gums, partially neutralized polyelectrolytes such as polyacrylic acid, polyimides, and alginates. In some circumstances, copolymer mixtures of the foregoing may also be suitable. The preferred polymers, however, are non-ionic or non-electrolyte hydrophilic polymers such as PEO, PVP, PAAm, HPC and HEC, or copolymers of these, because these materials do not contain large numbers of ionizable moieties which would compete as charge carriers with the drug to be iontophoretically administered. Commercial forms of HPC are preferred such as Klucel HF NF. The polymer is chosen so that fully dissolved thickener is viscous enough to remain within the hydrated matrix. For example, with the preferred Klucel HF NF, a concentration between 1 and 1.5% in the hydrated matrix has sufficient viscosity.

It may also be desirable to include various agents such as solvents, surfactants, wetting agents, or other excipients in the solution. A surfactant has been found particularly useful to assist in rapid hydration of the hydratable matrix element. Hence, it has been found useful to add Tween 20 nonionic surfactant (available from ICI America) to the hydratable matrix element. The addition of a surfactant such as Tween 20 has been found to aid the rate of wetting during hydration. Although for purposes of brevity the following discussion is primarily directed to the use of Tween 20, it should be understood that other surfactants could also be used in place of Tween 20 in those situations where a surfactant is desired. Examples of other useful surfactants are Neodol 91-6 (a nonionic primary alcohol ethoxylate manufactured by Shell Chemical Co.); Tergitol 15-S-7 (a nonionic secondary alcohol ethoxylate manufactured by Union Carbide); Pluronic Poloxamer F68 or F127 made by BASF; and Duponol C or Duponol XL (anionic sodium lauryl sulfates manufactured by Dupont Chemical Corp.). It is desirable that the surfactant be substantially nonionic, although small quantities of ionic moieties can be permitted.

In a presently preferred embodiment of hydratable matrix element, the thickener KLUCEL HF, manufactured by Aqualon Company, 1313 No. Market Street, Wilmington, Del., and the surfactant TWEEN-20 are impregnated into a spin-laced rayon/polyester material, SONATRA 8423, manufactured by E.I. DuPont De Nemours & Co., Textile Fibers Dept., Wilmington, Del. In dry form, this composition contains 15% Klucel and 15% Tween 20 by weight. Hydration of 8 $cm^2$ of this composition with 0.5 ml water forms a solution within the SONATRA which is about 1.5% KLUCEL and 1.5% TWEEN by weight.

Figure 4:
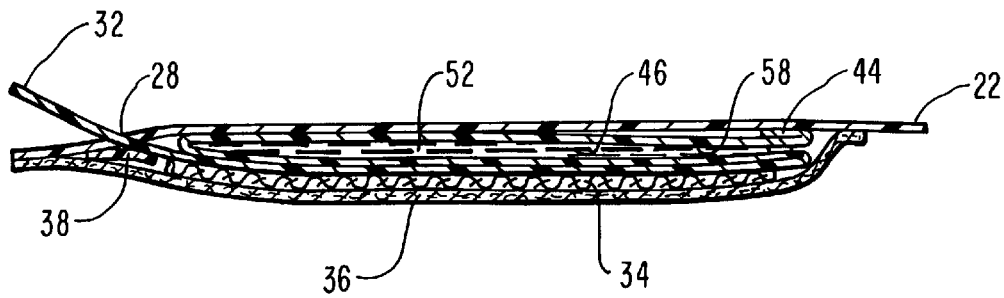
FIG. 4 is a cross-section of a portion of the preferred embodiment taken along the line 4—4 of FIG. 1 prior to activation of the hydration assembly.
Figure 5:
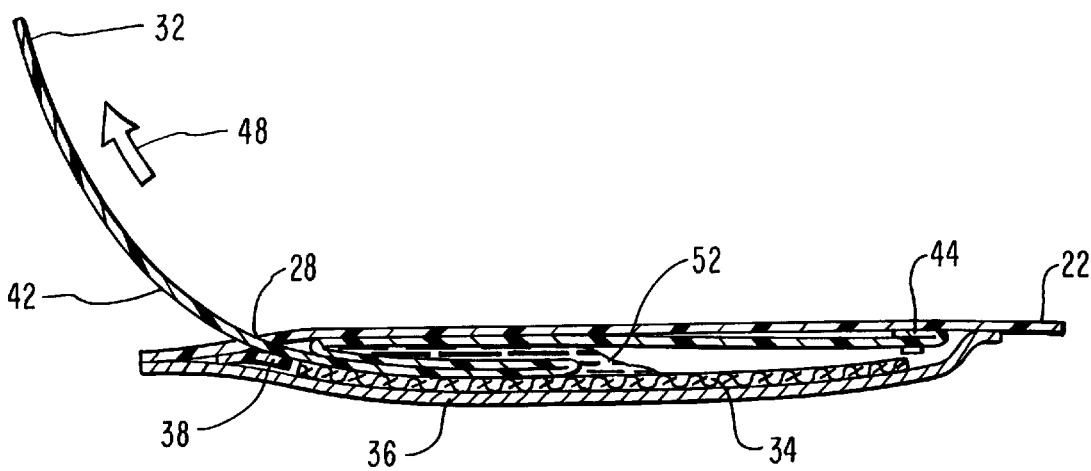
FIG. 5 is a cross-sectional view of the preferred embodiment corresponding to FIG. 4 but illustrating the hydration process in progress.
Figure 6:
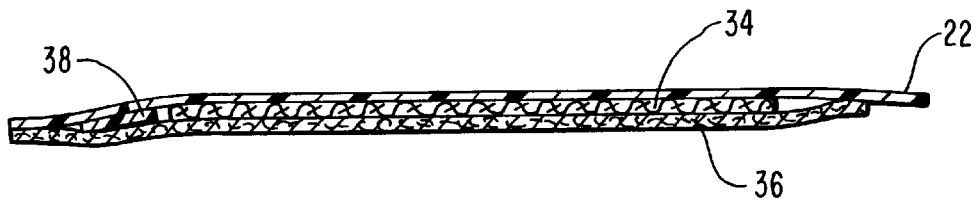
FIG. 6 is a cross-sectional view of the preferred embodiment corresponding to FIGS. 4 and 5 following completion of the hydration process.

As shown in FIG. 3, the components associated with the hydratable matrix element in the preferred embodiment are the slot seal element 38, the removable hydration assembly 58, and the optional porous cover membrane 36. The porous cover membrane and slot seal element have been detailed above. The removable hydration assembly will be better understood by reference to FIGS. 7–10, depicting formation of the hydration assembly and FIGS. 4–6, depicting the hydration process.

Accordingly, attention should now be directed to FIGS. 7, 8, 9, and 10, wherein the process for forming the hydration assembly of the preferred embodiment is illustrated in simplified detail. FIG. 7 shows a strip element 42 which serves as a component of the hydration assembly of the presently preferred embodiment illustrated in FIGS. 1–6. The strip element material is liquid-impermeable and has a surface capable of being reversibly sealed to itself using a suitable sealing method such as heat sealing, crimping, or a pressure sensitive adhesive. For example, a suitable material would be a high barrier, heat seal peelable, puncture-resistant packaging material such as TPC-0760 manufactured by Tolas Health Care Packaging, Feasterville, Pa. TPC-0760 comprises polyester film, LD polyethylene, foil, ionomer, and a heat seal coating.

As shown in FIG. 7, the strip element is preferably a single strip of suitable material. It should be understood, however, that the strip material could be formed in an alternative fashion without departing from the teachings set forth herein. One end of the strip element in FIG. 7 has been folded to create an end flap 44 for use in attaching the strip element to the multilaminate mounting element, as will be described below. The strip element is further illustrated as having a first portion 42A and a second portion 42B.

FIG. 8 shows the first portion 42A of the strip element folded so as to face the second portion 42B of the strip element. Also shown is another portion of the strip element designated 42D. The edges of the first and second portions are sealed together such that a pocket member 45 having one open end is formed. In FIG. 8, the sealed edges of the first and second portions are designated by reference numeral 42C. Because the pocket member 45 must later be unsealed, seal 42C must be accomplished in a manner which permits unsealing by operation of reasonable force, for example, 400–600 grams. Suitable strip materials and sealing methods were discussed above.

Figure 9:
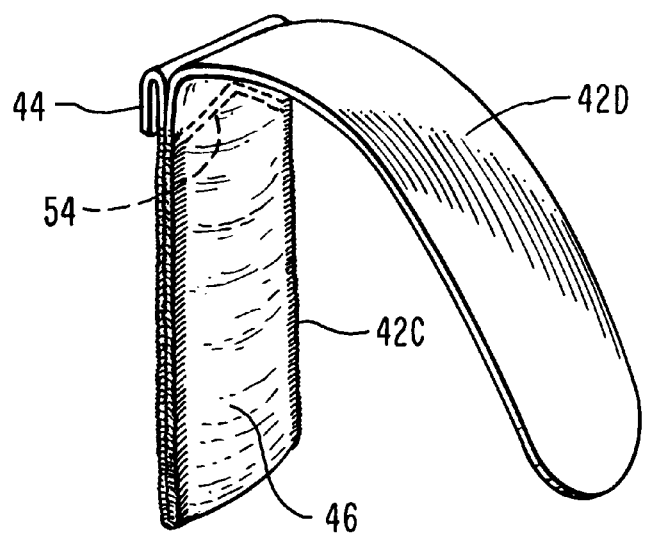
FIG. 9 illustrates the filled and sealed liquid-storage component of the preferred embodiment.

As shown in FIG. 8, the desired hydrating liquid 52 is delivered through the open end of the pocket member 45, schematically illustrated in FIG. 8 by means of a dropper 50. Once the desired hydrating liquid is delivered, the open end of the pocket member is sealed closed thereby forming a sealed liquid-storage component 46. FIG. 9 depicts this sealing by means of a dotted line 54 illustrating a chevron-shaped seal. The advantage of using a chevron-shaped seal is that unsealing can begin substantially at a single point rather than along a broad area, thereby lessening the force required to commence opening of the liquid-storage member. It should be appreciated, however, that other patterns which ensure ease of unsealing could also be used. Although a chevron-shaped seal is preferred, it should be understood that a straight seal, or seal of other shape, could be used as long as the seal could be opened with reasonable force.

Figure 10:
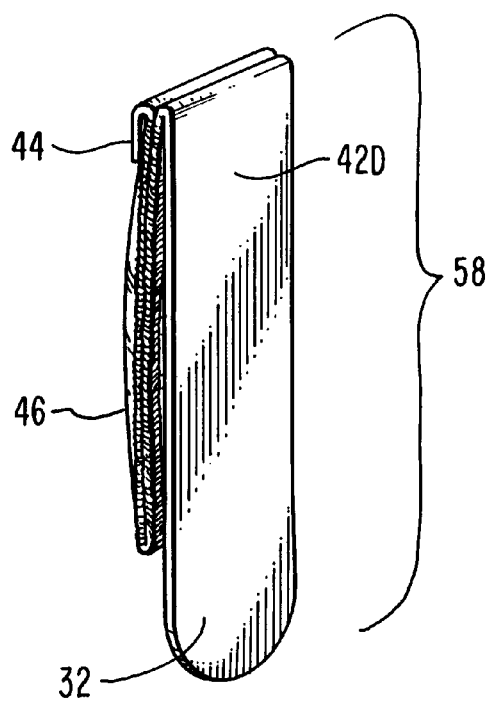
FIG. 10 illustrates the hydration assembly of the preferred embodiment.

A completed hydration assembly 58 is illustrated in FIG. 10. The third portion 42D of the strip element has been folded to a position aligned with the sealed liquid-storage component 46. As shown in FIG. 10, because the third portion of the strip element is longer than the second portion, the third portion extends beyond the second portion thereby forming tab member 32. The result is a hydration assembly 58 which assumes a substantially flattened Z-shape configuration as best seen in FIG. 10.

Referring once again to FIG. 4, hydration assembly 58 is advantageously positioned within the bioelectrode system by affixing end flap 44 to the multilaminate mounting element 22 so as to dispose the sealed liquid-storage component 46 over the hydratable matrix element 34. Accordingly, activation of the hydration assembly permits the hydrating liquid 52 to be properly deposited upon the hydratable matrix element. The various components of the bioelectrode system are preferably assembled as shown in FIG. 4 so as to form a cavity between the multilaminate mounting element 22 and the porous cover membrane 36. The hydration assembly 58 comprising the sealed liquid-storage component 46 with contained hydrating liquid 52, the slot seal element 38, and the hydratable matrix element 34 are positioned within the cavity. Tab member 32 extends through a cut-out slot 28 formed in the multilaminate mounting element to the exterior of the cavity. The cut-out slot 28 is more clearly seen in FIGS. 1 and 3.

The process of hydration is illustrated in progress in FIG. 5. The arrow identified by reference numeral 48 in FIG. 5 depicts the application of a force to the tab member 32 which results in movement of the tab member in the indicated direction. Movement of the tab member causes progressive unsealing of the attached liquid-storage component 46 within the cavity beginning at the chevron-shaped sealed end, not shown, as described above. As the liquid-storage component unseals, the portion of the strip element forming one side of the liquid-storage component is turned inside out such that the wet surface, i.e., the surface which had been in contact with the contained hydrating liquid, is wiped against the surface of the hydratable matrix element. This progressive unsealing and inverting causes the hydrating fluid 52 to be continuously released and uniformly transferred along the length and width of the surface of the hydratable matrix element 34.

FIG. 5 also illustrates the process of removing the hydration assembly 58 from within the cavity in progress. As the sealed liquid-storage component unseals, the strip element 42 is withdrawn from the cavity. Once the liquid-storage component is completely unsealed, the remaining portion of the strip element including the end flap 44, which is attached to the multilaminate mounting element, will remain within the cavity between the multilaminate mounting element and the hydratable matrix element. Further operation of the tab member will cause detachment of the end flap 44 such that the remaining portion of the strip element can be withdrawn from within the bioelectrode system. During this removal, the remaining portion of the strip element, one surface of which had formed an inner surface of the liquid-storage component contacting the hydrating liquid, will be wiped against the surface of the matrix element such that any remaining hydrating liquid is also transferred to the matrix element.

As can be seen in FIG. 6, after the hydrating fluid has been completely transferred and the entire hydration assembly has been withdrawn, only the multilaminate mounting element 22, the now-hydrated matrix element 34, the porous cover membrane 36, and the slot seal element 38 remain within the illustrated portion of the preferred bioelectrode system. As described above, the slot seal element is positioned between the now-hydrated matrix element and the cut-out slot to prevent leakage of medicament or electrolyte solution through the cut-out slot.

The hydration process illustrated in FIGS. 4–6 can be summarized as follows. The initial "dry" state of the preferred bioelectrode system of the present invention is shown in FIG. 4. The multilaminate mounting element 22 and the porous cover membrane 36 form a cavity surrounding the hydratable matrix element 34 and the sealed liquid-storage component 46 containing the hydrating liquid 52. The hydration assembly 58 is attached to the surface of the multilaminate mounting element by end flap 44. The tab member 32 protrudes from the cut-out slot 28 in the multilaminate mounting element. The hydration process begins, as shown in FIG. 5, when force is applied to tab member 32 causing the sealed liquid-storage component to become progressively unsealed commencing at the chevron-shaped sealed end, not shown. As the liquid-storage component is progressively unsealed, the hydrating liquid is progressively released directly onto the surface of the hydratable matrix element. In this manner, as the liquid-storage component is progressively opened, its interior surface, wetted by exposure to the stored hydrating liquid, is inverted, i.e., turned inside out, and is simultaneously wiped against the surface of the hydratable matrix element. This unsealing, opening, inverting, and wiping action ensures complete, rapid and substantially uniform distribution and transfer of the hydrating liquid across the entire surface of the hydratable matrix.

In addition to providing rapid, complete, and uniform transfer of the hydrating liquid onto the surface of the hydratable matrix element, operation of the tab member also progressively removes the entire hydration assembly from within the bioelectrode system. As the tab member is pulled, the liquid-storage component is substantially simultaneously unsealed, inverted, and withdrawn from the cavity. When the liquid-storage component is completely unsealed, further operation of the tab member causes the end flap 44 of the strip element to detach from the multilaminate mounting element such that the entire spent hydration assembly element can be removed from the bioelectrode system. Accordingly, FIG. 6 illustrates the "hydrated" form of the preferred bioelectrode system.

It has been assumed in the foregoing discussion that medicament is stored in dry form as a component of the hydratable matrix element. It should be appreciated that medicament may alternatively be stored in hydrated form within the hydrating liquid-storage member. Another alternative would be to store one or more forms of medicaments in both the hydratable matrix element and within the hydrating liquid. Such a configuration may be particularly useful with multiple medicaments that may cross-react during storage or to increase concentrations at the time of use.

Figure 11:
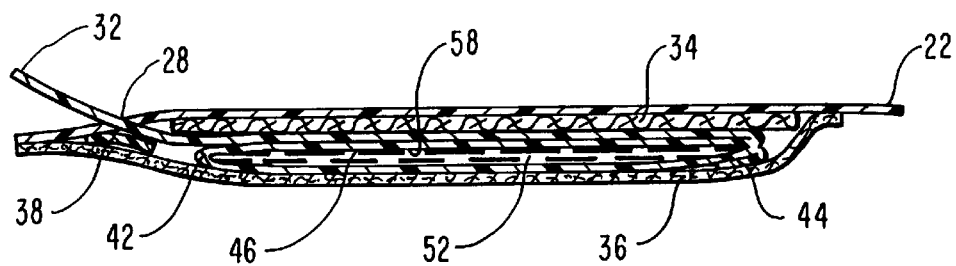
FIG. 11 is a cross-sectional view of a portion of an alternative embodiment of the present invention shown prior to activation of the hydration assembly.

It should be understood that although FIGS. 1–6 depict a presently preferred embodiment of a bioelectrode system, other embodiments would come within the scope of the teachings set forth herein. For example, FIG. 11 illustrates a cross-sectional view of a portion of an alternative embodiment of the present invention at a time prior to hydration. It can be seen that FIG. 11 corresponds to FIG. 4 except that the position of the hydration assembly and the hydratable matrix element within the cavity are reversed. Accordingly, as in FIG. 4, the initial "dry" state of the embodiment is illustrated wherein the multilaminate mounting element 22 and the porous cover membrane 36 form a cavity enclosing the hydratable matrix element 34 and the sealed liquid-storage component 46 containing the hydrating liquid 52. The hydration assembly 58 is attached to the porous cover membrane 36 by the end flap 44. The tab member 32 is seen to protrude from the cut-out slot 28 in the multilaminate mounting element. The slot seal element 38 is aligned with the cut-out slot and positioned between the hydration assembly 58 and the porous cover membrane 36. It should be understood that the hydration assembly could alternatively be attached to the multilaminate mounting element by the end flap and tab member could protrude from a cut-out slot formed in the porous cover membrane, if desired. Operation of the hydration means in this alternative embodiment proceeds in the manner illustrated for the preferred embodiment in FIGS. 5 and 6 with the only difference being that the relative positions of the hydration assembly and the hydratable matrix element are reversed.

Figure 12:
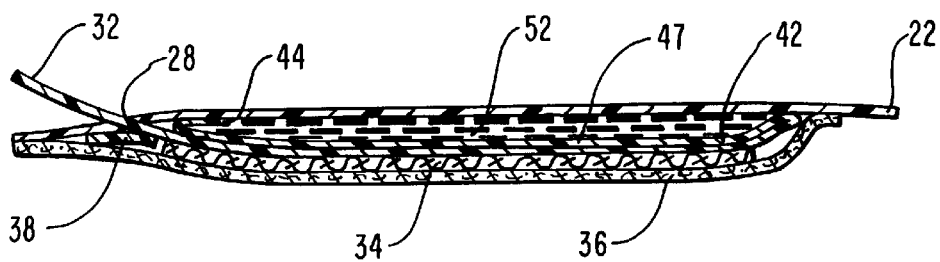
FIG. 12 is a cross-sectional view of a portion of another alternative embodiment of the present invention shown prior to activation of the hydration assembly.

FIG. 12 is a cross-sectional view of a portion of yet another alternative embodiment of the present invention shown prior to hydration. This figure corresponds to FIG. 4 except that the sealed hydrating liquid-storage component 47, rather than being formed by folding a first portion of the strip element to face a second portion of the strip element and sealing the edges of the portions together, is formed by sealing the edges of a first portion of the strip element to the facing surface of the multilaminate mounting element 22. The hydrating liquid is introduced into the pocket formed between the first portion of the strip element and the multilaminate mounting element and sealed closed in the manner described above for the preferred embodiment. Accordingly, as in FIG. 4, the initial "dry" state of the embodiment is illustrated wherein the multilaminate mounting element 22 and the porous cover membrane 36 enclose the hydratable matrix element 34 and the alternative embodiment of the sealed liquid-storage component 47 containing the hydrating liquid 52. The strip element 42 is attached to the multilaminate mounting element by the end flap 44 near the cut-out slot. The tab member 32 protrudes from the cut-out slot 28 in the multilaminate mounting element. The slot seal element 38 is aligned with the cut-out slot and positioned between the multilaminate mounting element and the porous cover membrane. It should be understood that operation of the hydration means in this alternative embodiment proceeds in the manner illustrated for the preferred embodiment in FIGS. 5 and 6 with the only difference being that, once the liquid-storage component is completely unsealed, only the end flap 44 remains within the cavity between the multilaminate mounting element and the now-hydrated matrix element. As with the above-described embodiments, further operation of the tab member detaches the end flap such that the entire hydration assembly can be withdrawn completely from the cavity.

FIG. 13 illustrates an alternative embodiment wherein tab member 32, rather than extending through a cut-out slot in the multilaminate mounting element, merely extends from between the multilaminate mounting element and the hydratable matrix element. Accordingly, rather than forming a cut-out slot within the multilaminate mounting element, the multilaminate mounting element and the hydratable matrix element are secured to each other in a manner providing an opening for protrusion of the tab member therethrough. It should also be understood that, although each hydration assembly is illustrated as having a separate tab member in the preferred embodiment, an alternative embodiment, as shown in FIG. 13, could combine the tab members into one pull-tab member 33.

Figure 14:
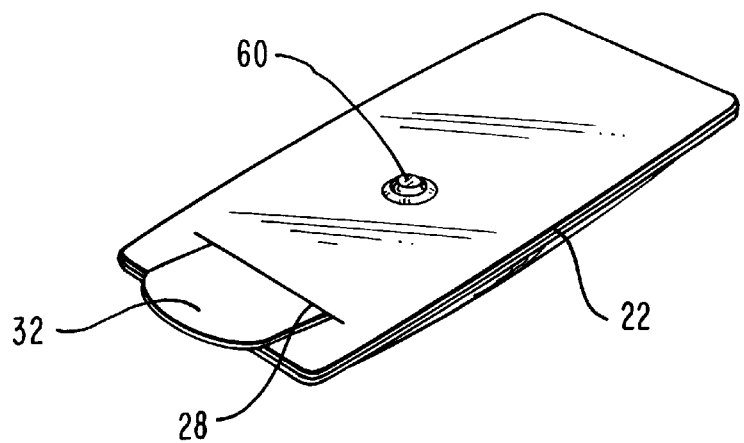
FIG. 14 is a perspective top view of a single electrode embodiment of the present invention.

It should be understood that the hydration assembly disclosed above may be utilized within a single bioelectrode as well as within an integral bioelectrode system of the type illustrated. FIG. 14 shows such a top view of single bioelectrode in accord with the present invention having a multilaminate mounting element 22 with a cut-out slot 28 through which the tab member 32 of the hydration assembly, not shown, protrudes. In this embodiment, a connector 60 serves to connect the hydratable matrix element, not shown, to an external electrical current, also not shown. The connector 60 is shown as a "nipple" type connector, however, it should be understood that other types of connectors would also be suitable.

The present invention may be embodied or utilized in other specific forms or manners without departing from its spirit or essential characteristics. The described embodiments and methods are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A hydration assembly for use in hydrating a hydratable matrix element of an iontophoresis bioelectrode, said hydration assembly comprising:

a hydrating liquid;

hydrating liquid isolation means for maintaining said hydrating liquid in isolation from said hydratable matrix element until it is desired to hydrate the hydratable matrix element, said hydrating liquid isolation means comprising a first portion reversibly sealed to a strip element to define a liquid-storage component therebetween; and hydration activation means for effecting progressive release of said hydrating liquid from said liquid-storage component, said hydration activation means comprising a strip extension, said strip extension having a first end and a second end, said first end being continuous with said strip element and said strip extension being folded over at said first end such that said strip extension is folded upon, adjacent to, and aligned with said strip element over substantially the entire length of said strip element, and said second end having an accessible tab member continuous with said strip extension;

wherein operation of said tab member causes progressive movement of said strip extension away from said liquid-storage component, progressive inverting of said strip element upon itself, and progressive reversing of the seal between the strip element and the first portion.

2. A hydration assembly as defined in claim 1 wherein the strip element comprises a liquid-impermeable material.

3. A hydration assembly as defined in claim 1 wherein the first portion is continuous with said strip element and said first portion is folded upon, facing, and aligned with said strip element such that said first portion, said strip element, and said strip extension are foldable positioned in a substantially flattened z-shaped configuration and said first portion is reversibly sealed to said strip element to form a pocket member having an open end, which open end is filled with hydrating liquid and, subsequently, reversibly sealed closed.

4. A hydration assembly as defined in claim 3 wherein the seal closing the open end of said pocket member is applied in a chevron-shape to permit unsealing to commence at a single point.

5. A hydration assembly as defined in claim 1 wherein the first portions and the strip element are sealed by heat.

6. A hydration assembly as defined in claim 1 wherein the first portion and the strip element are sealed with pressure sensitive adhesive.

7. A hydration assembly as defined in claim 1 wherein the first portion and the strip element are sealed by crimping.

8. A hydration assembly as defined in claim 1 wherein the first portion further comprises an end flap.

9. A hydration assembly as described in claim 1 further comprising a mounting element, said mounting element having a surface comprising said first portion of said hydrating liquid isolation means wherein said strip element is reversibly sealed to a portion of said surface to form a pocket member having an open end, which open end is filled with hydrating liquid and, subsequently reversibly sealed closed.

* * * * *